(12) United States Patent
Keum et al.

(10) Patent No.: US 9,763,923 B2
(45) Date of Patent: Sep. 19, 2017

(54) COMPOSITION FOR REDUCING SENESCENCE OF CELL OR SUBJECT INCLUDING BRAF INHIBITOR AND USE THEREOF

(71) Applicant: Samsung Electronics Co., Ltd., Suwon-si, Gyeonggi-do (KR)

(72) Inventors: Jungwon Keum, Yongin-si (KR); Joontae Park, Seoul (KR); Chulwon Jung, Seoul (KR); Sangchul Park, Seongnam-si (KR); Youngsam Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/144,463

(22) Filed: May 2, 2016

(65) Prior Publication Data

US 2016/0317518 A1 Nov. 3, 2016

(30) Foreign Application Priority Data

Apr. 30, 2015 (KR) ........................ 10-2015-0062012

(51) Int. Cl.
| | | |
|---|---|---|
| *A61K 31/4439* | (2006.01) | |
| *A61K 31/428* | (2006.01) | |
| *A61K 31/437* | (2006.01) | |
| *A61K 8/00* | (2006.01) | |

(52) U.S. Cl.
CPC ............ *A61K 31/4439* (2013.01); *A61K 8/00* (2013.01); *A61K 31/428* (2013.01); *A61K 31/437* (2013.01)

(58) Field of Classification Search
CPC .............. A61K 31/4439; A61K 31/437; A61K 9/0014; A61K 31/428
See application file for complete search history.

(56) References Cited

U.S. PATENT DOCUMENTS

| | | |
|---|---|---|
| 2006/0134068 A1 | 6/2006 | Dong |
| 2011/0150899 A1 | 6/2011 | Park et al. |
| 2012/0238023 A1 | 9/2012 | Eto et al. |
| 2013/0059851 A1 | 3/2013 | Garraway et al. |
| 2013/0064789 A1* | 3/2013 | Falini ................. C12Q 1/6886 424/85.4 |
| 2014/0057904 A1 | 2/2014 | Garcia-Echeverria et al. |

FOREIGN PATENT DOCUMENTS

| | | |
|---|---|---|
| KR | 2010-0013512 A | 2/2010 |
| KR | 2012-0064109 A | 6/2012 |

OTHER PUBLICATIONS

Tan et al (Biogerontology, 2014, 15:643-660).*
Carnahan et al., "Selective and Potent Raf Inhibitors Paradoxically Stimulate Normal Cell Proliferation and Tumor Growth, Molecular Cancer Therapeutics", 9(8): 2399-2410 (2010).
Hatzivassiliou et al.,"RAF inhibitors prime wild-type RAF to activate the MAPK pathway and enhance growth", *Nature*, 464: 431-435 (2010).
Heidorn et al., "Kinase-Dead BRAF and Oncogenic RAS Cooperate to Drive Tumor Progression through CRAF", *Cell*, 140(2):209-221 (2010).
Poulikakos et al., "RAF inhibitors transactivate RAF dimers and ERK signalling in cells with wild-type BRAF", *Nature*, 464: 427-430 (2010).

* cited by examiner

*Primary Examiner* — Sudhakar Katakam
(74) *Attorney, Agent, or Firm* — Leydig, Voit & Mayer, Ltd.

(57) ABSTRACT

Provided is a method of reducing senescence in a cell or subject, or treating or preventing a symptom or disease associated therewith, by administering a BRAF inhibitor to the cell or subject.

9 Claims, 9 Drawing Sheets

DMSO

SB590885

COMPOSITION FOR REDUCING SENESCENCE OF CELL OR SUBJECT INCLUDING BRAF INHIBITOR AND USE THEREOF

CROSS-REFERENCE TO RELATED APPLICATION

This application claims the benefit of Korean Patent Application No. 10-2015-0062012, filed on Apr. 30, 2015, in the Korean Intellectual Property Office, the entire disclosure of which is hereby incorporated by reference.

BACKGROUND

1. Field

The present disclosure relates to a composition for reducing a senescence level of a cell or subject, a method of reducing the senescence level in the cell or subject using the composition, and a method of preventing or treating symptoms or diseases related to senescence in the cell or subject.

2. Description of the Related Art

Senescence or aging is a degenerative phenomenon that occurs over time. In the case of humans, physiological activities may deteriorate with aging, but activities of some enzymes or secretion of some hormones may increase. Senescence of a cell may be defined as a permanent halt of cellular division. Replicative senescence or cellular senescence has been observed as an aging model at the cell level. When cells are continuously cultured, cells divide multiple times, but cells can no longer divide as they get older. In fact, senescent cells are resistant against programmed cell death, and some senescent cells remain in a non-dividing state for several years.

BRAF or B-RAF is a member of the Raf kinase family and is a serine/threonine-specific protein kinase that drives cell growth or proliferation. BRAF mutations are found in some of human cancers, and thus BRAF inhibitors have been developed as anti-cancer drugs.

Thus, there is a need for a composition and method of reducing senescence of a cell or subject.

SUMMARY

Provided is a method of reducing senescence in a cell or subject comprising administering a BRAF inhibitor to the cell or subject. Also provided is a method of preventing or treating a symptom or disease caused by senescence of a cell, comprising administration of a BRAF inhibitor to the cell or subject in need thereof. Related compositions and methods also are provided

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
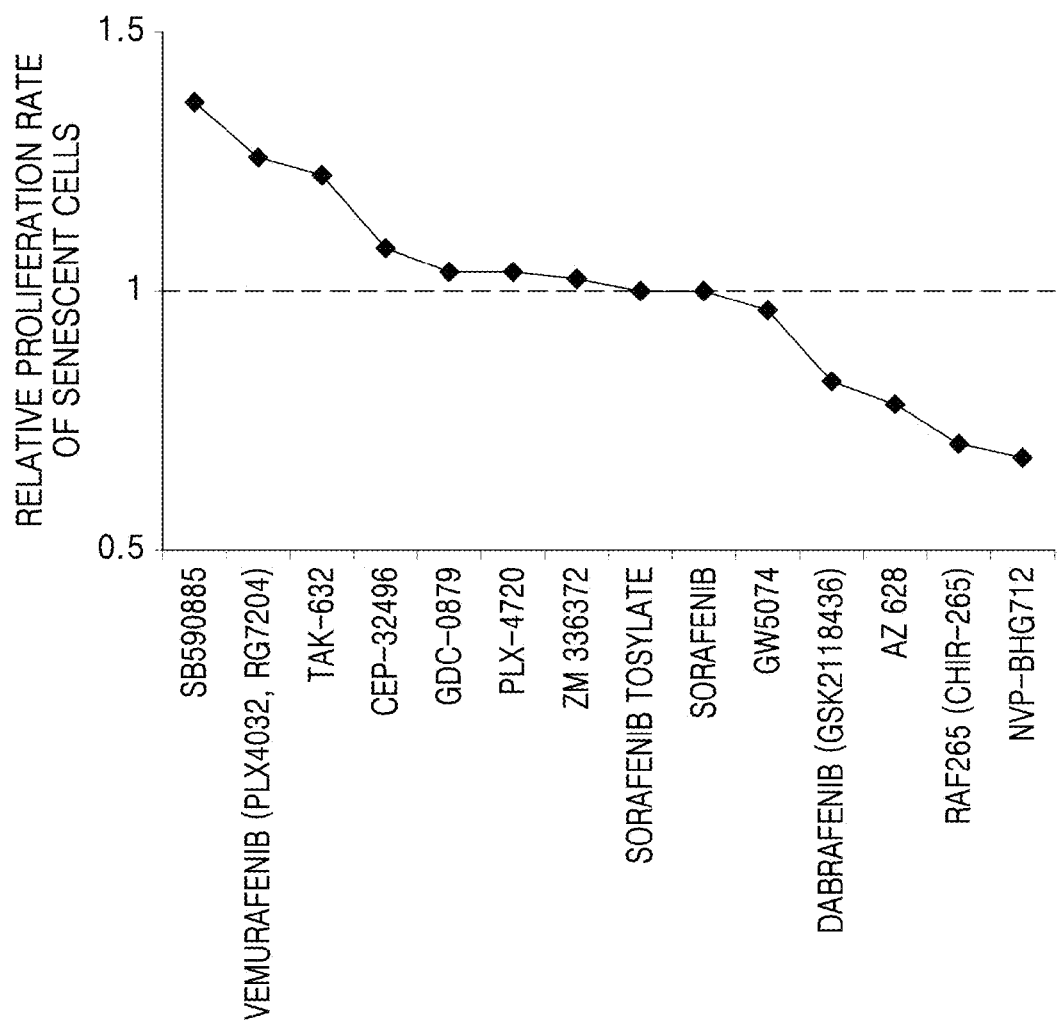
FIG. 1 is a graph showing relative proliferation rates of senescent cells in the presence of various BRAF inhibitors.

An aspect provides a composition for reducing a senescence level of a cell or subject including a BRAF inhibitor.

The term "BRAF" is used interchangeably with "B-RAF". B-RAF is a serine/threonine-specific protein kinase that drives cell growth or proliferation. BRAF protein may be, for example, a protein encoded by a nucleotide sequence of GenBank Accession No. NM_004333 or a protein having an amino acid sequence of GenBank Accession No. NP_004324. In a mouse, BRAF protein may be, for example, a protein encoded by a nucleotide sequence of GenBank Accession No. NM_139294 or a protein having an amino acid sequence of GenBank Accession No. NP_647455. In a human, BRAF protein may be a protein consisting of 766 amino acids. BRAF protein may be a protein including conserved region (CR)1 as a Ras-GTP-binding self-regulatory domain, CR2 as a serine-rich hinge region, and CR3 as a catalytic protein kinase domain that phosphorylates a consensus sequence on protein substrates. In its active conformation, BRAF protein forms dimers via hydrogen-bonding or electrostatic interactions of its kinase domains.

The BRAF inhibitor may be an agent that inhibits activity of BRAF protein or expression thereof. The agent that inhibits activity of BRAF protein may be an agent that inhibits activity of mutated BRAF protein. The agent that inhibits activity of BRAF protein may be a compound, a nucleic acid, an ion, an antibody, an antipeptide, or a combination thereof. The agent that inhibits activity of BRAF protein may be a selective BRAF protein activity inhibitor or a non-selective BRAF protein activity inhibitor. The agent that inhibits expression of BRAF protein may be a small interfering RNA (sRNA), a microRNA (miRNA), an antisense oligonucleotide, or a combination thereof.

The BRAF inhibitor may be SB590885, vemurafenib (PLX4032, RG7204), TAK-632, CEP-32496, GDC-0879, PLX-4720, ZM 336372, Sorafenib tosylate, Sorafenib, GW5074, Dabrafenib (GSK2118436), AZ 628, RAF265 (CHIR-265), NVP-BHG712, Encorafenib (LGX818), a pharmaceutically acceptable salt, stereomer, derivative, or solvate thereof, or a combination thereof.

The BRAF inhibitor may be in the form of a pharmaceutically acceptable salt thereof. The salt may include acid addition salts commonly used in the pharmaceutical field, for example, in the field of diseases related to cellular senescence. The acid addition salt includes, for example, salts derived from inorganic acids such as hydrochloric acid, bromic acid, sulfuric acid, sulfamic acid, phosphoric acid, or nitric acid; and salts derived from organic acids such as acetic acid, propionic acid, succinic acid, glycolic acid, stearic acid, citric acid, maleic acid, malonic acid, methanesulphonic acid, tartaric acid, malic acid, phenylacetic acid, glutamic acid, benzoic acid, salicylic acid, acetoxybenzoic acid, fumaric acid, toluenesulfonic acid, oxalic acid, or trifluoroacetic acid. Further, the salt includes ordinary metal salts, for example, salts derived from metals such as lithium, sodium, potassium, magnesium, or calcium. The acid addition salts or metal salts may be prepared by an ordinary method.

The BRAF inhibitor may be in the form of a stereomer thereof. The stereomer may be an enantiomer or a diastereomer. The BRAF inhibitor may be a stereoisomerically pure form or a mixture of one or more stereomers, for example, a racemic mixture. Isolation of a particular stereomer may be performed by any ordinary method known in the art.

The BRAF inhibitor may be in the form of a derivative thereof. The derivative may be a compound that is obtained by chemical replacement of a part of the BRAF inhibitor compound with another atom or group of atoms.

The BRAF inhibitor may be in the form of a solvate thereof. The solvate means a complex or aggregate that is formed by one or more molecules of a solute, i.e. the BRAF inhibitor, or a pharmaceutically-acceptable salt, stereomer, or derivative thereof, and one or more molecules of a solvent. The solvate may be a complex or aggregate that is formed with, for example, water, methanol, ethanol, isopropanol, or acetic acid.

The cell may be, for example, a nerve cell, an immune cell, an epithelial cell, a reproductive cell, a muscle cell, or a cancer cell. The cell may be a fibroblast or an early senescent cell. The early senescent cell may be a cell derived from a progeria patient.

The subject may be a mammal, for example, a human, cattle, a horse, a pig, a dog, sheep, a goat, a rat, a mouse, a rabbit, or a cat.

Senescence refers to an array of changes that occurs over time. Compared to a reference cell or subject (e.g., a cell of the same type known to be non-senescent), a senescent cell or subject is defined as a cell or subject that shows a decrease in cell proliferation ability, an accumulation of lipofuscin (e.g., increase in lipofuscin accumulation), an increase in β-galactosidase activity, an increase of mitochondrial-derived reactive oxygen species, or a combination thereof, or shows a process that causes those described above. The senescent cell or subject may further show a decrease in autophagy activity or a decrease in mitochondrial membrane potential, or shows a process that causes those described above. Compared to a reference cell or subject (e.g., a known senescent cell or subject), a young, non-senescent cell or subject may show an increase in cell proliferation ability, a decrease in lipofuscin accumulation, a decrease in β-galactosidase activity, or a combination thereof. For example, a cell having a doubling time that is twice or more, three times or more, four times or more, five times or more, six times or more, seven times or more, nine times or more, ten times or more, fifty times or more, or a hundred times or more than that of a cell passaged twice may be defined as a senescent cell. In the case of a human, a cell that is taken from a person about 30 years old or older, about 40 years old or older, about 50 years old or older, about 60 years old or older, about 70 years old or older, about 80 years old or older, about 90 years old or older, about 100 years old or older may be defined as a senescent cell.

The reduction of the senescence level of a cell or subject may be delaying senescence of the cell or subject, preventing the cell or subject from senescence, or transforming the senescent cell or subject into a young cell or subject. For example, the reduction of the senescence level of a cell or subject may include increasing a proliferation ability of the cell, decreasing β-galactosidase activity, decreasing lipofuscin accumulation, decreasing mitochondrial-derived reactive oxygen species, or a combination thereof. The reduction of senescence level of a cell or subject may include increasing autophagy activity, increasing mitochondrial membrane potential, or a combination thereof. The increasing of cell proliferation ability may be a decrease of a cell doubling time or an increase of cellular division times. The β-galactosidase may be a β-galactosidase related to senescence.

The composition may be a composition for preventing or treating a symptom or disease related to senescence of a cell or subject. The symptom or disease related to senescence of a cell or subject may be skin wrinkle, slow scar regeneration, degenerative brain disease (e.g., Alzheimer's disease, Parkinson's disease, and dementia), stroke, diabetes (e.g., type 2 diabetes), arthritis, atherosclerosis, heart disease, alopecia, osteoporosis, sarcopenia, progeria, lysosome storage disease, or a combination thereof. The symptom or disease related to senescence of a cell or subject may be a disease related to lipofuscin accumulation. Lipofuscin is a yellow-brown autofluorescent pigment granule in a cell. Lipofuscin is used as a senescence index and is referred to as an aging pigment. Accumulation of lipofuscin may be found on the retina, liver, kidney, or heart of an old person or patient who suffer from a wasting disease for a long period of time. The disease associated to lipofuscin accumulation may be neuronal ceroid lipofuscinoses (NCL), macular degeneration, neurofibrillary tangles, brown atrophy of the heart, Alzheimer's disease, Parkinson's disease, amyotrophic lateral sclerosis (ALS), acromegaly, denervation atrophy, lipid myopathy, chronic obstructive pulmonary disease (COPD), melanosis coli, atherosclerosis, or a combination thereof.

The term "preventing", as used herein, refers to any action that suppresses or delays an onset of a symptom or disease related to senescence by administration of the composition. The term "treating", as used herein, refers to any action that improves or advantageously changes a symptom or disease related to senescence by administering the composition.

The composition may be a pharmaceutical composition. The composition may further include a pharmaceutically acceptable carrier. With regard to the composition, the "pharmaceutically acceptable carrier" refers to a material that is used in combination with an active ingredient to help an application of the active ingredient, generally an inert material. The carrier may include a general pharmaceutically acceptable excipient, additive, or diluent. The carrier may include, for example, one or more selected from a filler, a binder, a disintegrant, a buffer, a preservative, an antioxidant, a lubricating agent, a flavoring agent, a thickener, a coloring agent, an emulsifier, a suspending agent, a stabilizer, and an isotonizing agent.

The composition may include the BRAF inhibitor, or a pharmaceutically acceptable salt, stereomer, derivative or solvate thereof, or a combination thereof at a "therapeutically effective amount". With regard to the composition, the "therapeutically effective amount" refers to a sufficient amount which is therapeutically effective upon administered to a subject in a need of treatment. The effective amount may be determined according to factors including severity of disease, patient's age, weight, health conditions, sex, sensitivity to drug, drug administration time, administration route, discharge rate, treatment period, and drugs which are mixed or used in combination with the composition of the exemplary embodiment, and other factors which are well known in the medical field. The "effective amount" may be present in the composition in a range of about 0.01 mg to about 10,000 mg, about 0.1 mg to about 1000 mg, about 1 mg to about 100 mg, about 0.01 mg to about 1000 mg, about 0.01 mg to about 100 mg, about 0.01 mg to about 10 mg, or about 0.01 mg to about 1 mg.

The composition may be administered, for example, in a dose of about 0.001 mg/kg to about 100 mg/kg, about 0.01 mg/kg to about 10 mg/kg, or about 0.1 mg/kg to about 1 mg/kg for adults once a day, several times a day, or once every several days.

The composition may be administered orally, or parenterally, in which the parenteral administration may include intravenous administration, intraperitoneal administration, subcutaneous administration, rectal administration, and topical administration. Accordingly, the composition may be formulated in a variety of forms, such as a tablet, a capsule, an aqueous solution, or a suspension. An excipient such as lactose or corn starch, and a lubricating agent such as magnesium stearate may be commonly added to an oral tablet. In the case of a capsule for oral administration, lactose and/or dried corn starch may be used as a diluent. If there is a need of an aqueous suspension for oral administration, active ingredients may be combined with an emulsifier and/or a suspension. If needed, a certain sweetening agent and/or a flavoring agent may be added thereto. In the case of intraneural administration, intramuscular administration, intraperitoneal administration, subcutaneous administration, and intravenous administration, a sterilized solution of active ingredients is commonly prepared, and pH of thereof needs to be adjusted and buffered appropriately. In the case of intravenous administration, a total concentration of a solute needs to be adjusted to obtain an isotonic formulation. The composition may be an aqueous solution containing a pharmaceutically acceptable carrier such as brine at pH 7.4. The solution may be administered to intramuscular or intraneural blood flow of a patient via a local bolus injection.

The composition may further include one or more therapeutic agents for treating a disease related to senescence of a cell or subject.

Another aspect provides a method of reducing a senescence level of a cell or subject, including administration of the BRAF inhibitor to the cell or subject.

The BRAF, BRAF inhibitor, cell, subject, senescence, and reducing a senescence level of the cell or subject are the same as described above.

The subject may be a mammal, for example, a human, cattle, a horse, a pig, a dog, sheep, a goat, a rat, a mouse, a rabbit, or a cat. The subject may be a subject that suffers from a symptom or disease related to senescence or at risk of having the symptom or disease related to senescence.

The administration may be, for example, in a dose of about 0.001 mg/kg to about 100 mg/kg, about 0.01 mg/kg to about 10 mg/kg, or about 0.1 mg/kg to about 1 mg/kg for adults once a day, several times a day, or once every several days during a period of several days to one year. The administration may be carried out using a method that is known in the art. The administration may be carried out by using, for example, any method that allows a direct administration to a subject, such as oral administration, intravenous administration, intramuscular administration, transdermal administration, mucosal administration, intranasal administration, intratracheal administration, or subcutaneous administration. The administration may be topical or systemic administration. The administration may be topical administration to a tissue including senescent cells.

Still another aspect provides a method of preventing or treating a symptom or disease related to senescence in a cell or subject, including administration of the BRAF inhibitor to the cell or subject.

The BRAF, BRAF inhibitor, cell, subject, administration, senescence, symptom or disease related to senescence in the cell or subject, preventing and treating are the same as described above.

According to the composition for reducing a senescence level of a cell or subject, the method of reducing the senescence level in the cell or subject using the composition, and the method of preventing or treating a symptom or disease related to senescence in the cell or subject according to an exemplary embodiment, the senescence level of the cell or subject may be effectively reduced, and a symptom or disease related to senescence may be effectively prevented or treated.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Example 1. Proliferation Induction or Recovery of Senescent Cells by BRAF Inhibitor 1. Proliferation Induction of Senescent Cells by BRAF Inhibitor In order to examine whether senescent cells proliferate in response to treatment with BRAF inhibitors, human dermal fibroblast (HDF) M11 cells taken from an 11-year-old boy are cultured in Dulbecco's Modified Eagle's Medium (DMEM) containing a high concentration of glucose, glutamine, and pyruvate, and 10% (v/v) fetal bovine serum (FBS), and 1× penicillin/streptomycin at about 37° C. and 5% $CO_2$ atmosphere, thereby obtaining senescent cells. As for the senescent cells, cells that are passaged 35 times and whose doubling time is about 10 days or longer are used.

The prepared senescent cells are inoculated at a density of 1000 cells/well in a 96-well plate. The BRAF inhibitor is added to the inoculated cells at a final concentration of 5 µM. SB590885, vemurafenib (PLX4032, RG7204), TAK-632, CEP-32496, GDC-0879, PLX-4720, ZM 336372, Sorafenib tosylate, Sorafenib, GW5074, Dabrafenib (GSK2118436), AZ 628, RAF265 (CHIR-265), and NVP-BHG712 are used as BRAF inhibiting drugs. Cells treated with dimethyl sulfoxide (DMSO) (Sigma-Aldrich) alone are used as a negative control group. The medium is replaced with a fresh medium containing the drug or DMSO alone once every four days. About 3 weeks after initial addition of the drug, 0.1% (w/v) SYBR Green I (Life Technologies, Cat. No.

S-7563) is used to quantify DNA, and the number of cells is calculated from the DNA quantity measured.

The number of the senescent cells in the drug-treated group is compared to the number of the cells in the negative control group so as to calculate a relative proliferation rate. The relative proliferation rates of senescent cells treated with BRAF inhibitors to that of the negative control group are shown in FIG. 1.

As shown in FIG. 1, cells treated with SB590885, vemurafenib, or TAK-632 exhibited proliferation rates about 30% higher than the negative control group.

2. Effects of SB590885, Vemurafenib, and TAK-632 on Senescent Cells

The optimal concentrations of SB590885, vemurafenib, and TAK-632 which are found to show excellent proliferation effects on senescent cells are examined, and the levels of β-galactosidase as a senescence index are examined at the optimal concentrations.

The senescent cells prepared as described in 1 are inoculated at a density of 1000 cells/well in a 96-well plate. SB590885, vemurafenib, or TAK-632 is added to the cell culture at a concentration of 0.1 μM, 0.5 μM, 1.0 μM, 2.0 μM, or 5.0 μM. Cells treated with DMSO alone are used as a negative control group. As described in Example 1, the senescent cells are cultured for about 3 weeks in the presence of the drug.

Figure 2A:
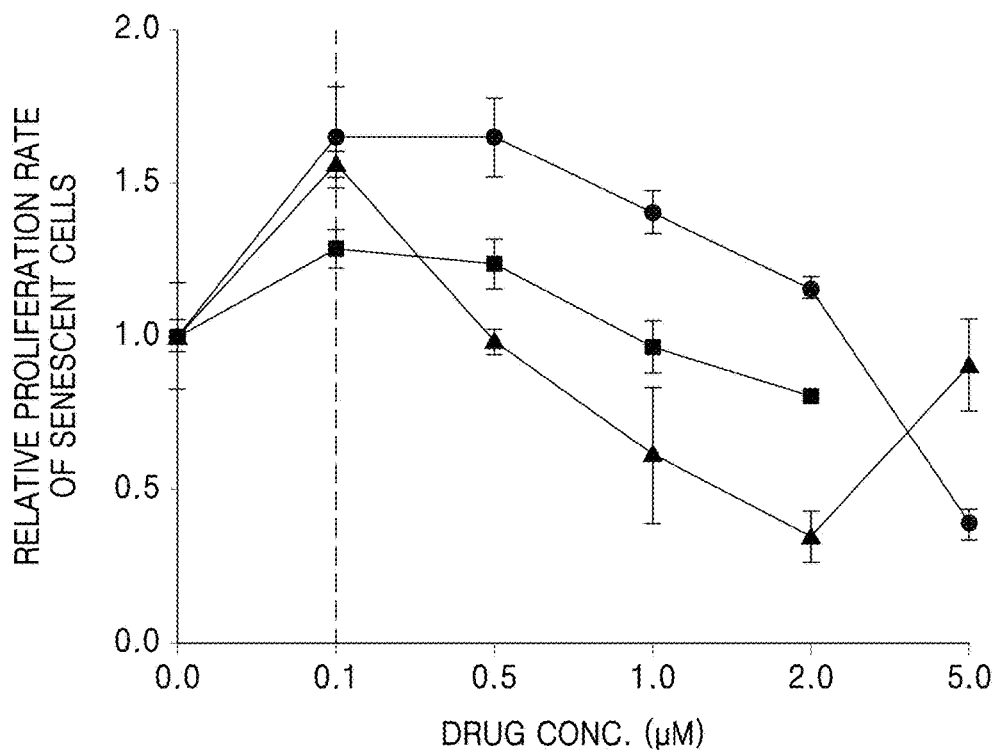
FIG. 2A is a graph showing relative proliferation rates of senescent cells according to concentrations (μM) of SB590885, vemurafenib, and TAK-632 as BRAF inhibitors (●: SB590885, ■: vemurafenib, ▲: TAK-632)

Then, SYBR Green I (Life Technologies, Cat. No. S-7563) is used to quantify DNA in the senescent cells thus cultured, and the number of cells is calculated from the DNA quantity measured. The number of the senescent cells in the drug-treated group is compared to the number of the cells in the negative control group so as to calculate a relative proliferation rate of the senescent cells treated with SB590885, vemurafenib, or TAK-632. The relative proliferation rates of the senescent cells to that of the negative control group are shown in FIG. 2A (●: SB590885, ■: vemurafenib, ▲: TAK-632). As shown in FIG. 2A, a high relative proliferation rate of the senescent cells is found in 0.1 μM SB590885.

Figure 2B:
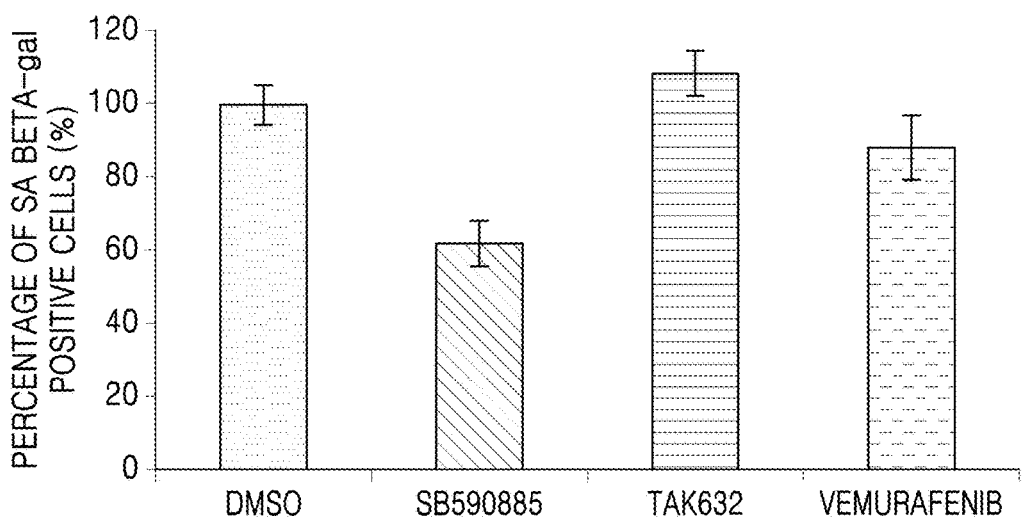
FIG. 2B is a graph showing percentages (%) of senescence-associated beta-galactosidase (SA β-gap-positive cells by treatment of SB590885, vemurafenib, and TAK-632, and FIG. 2C shows SA β-gal staining images of senescent cells cultured in the presence of SB590885 for about 11 days (Scale bar: 200 μm)
Figure 2C:
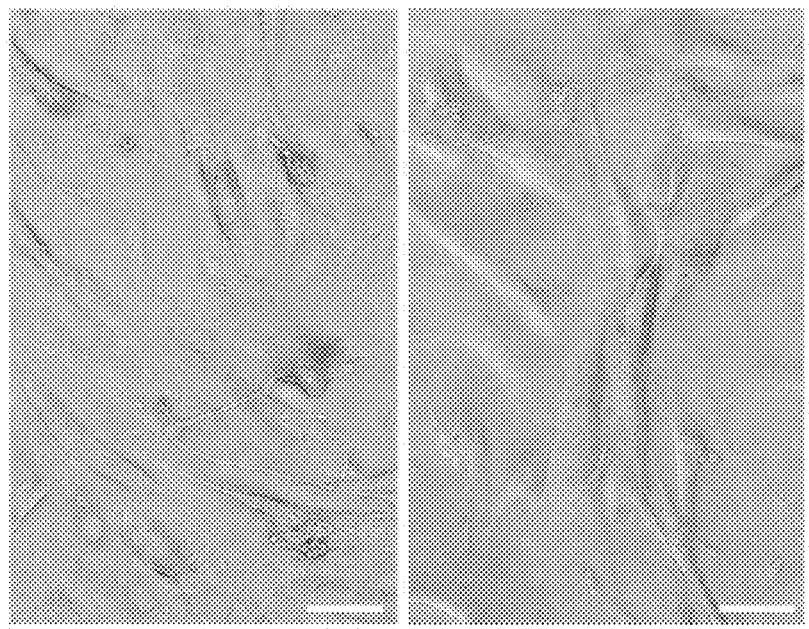
Figure 2C:
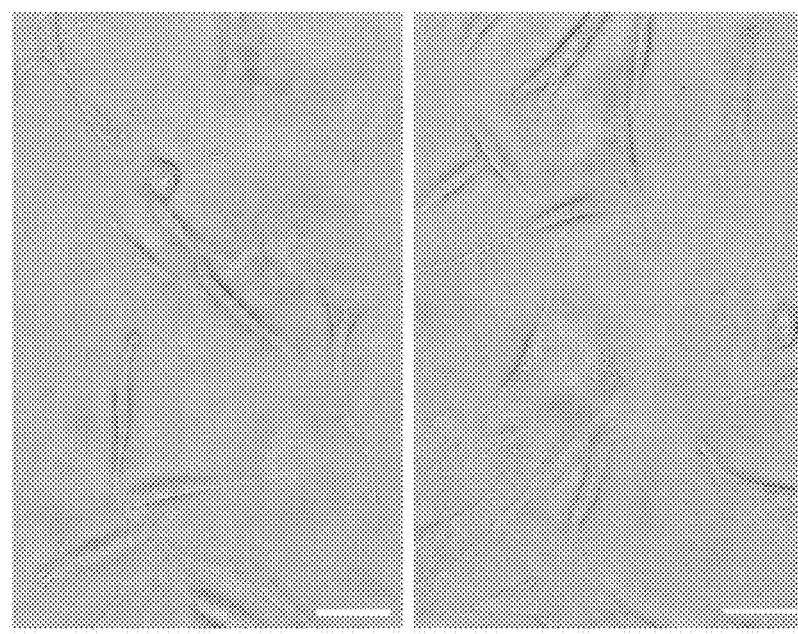

Senescent cells are stained blue with X-gal staining due to increased activity of senescence-associated beta-galactosidase (SA β-gal) which is a senescence index. In order to examine whether the senescence index level is reduced by drug treatment, the cultured senescent cells are stained using a cellular senescence assay kit (Cell Signaling Technology, Cat. No. 9860), and observed under a microscope to count the number of the cells stained blue. Percentages (%) of SA β-gal-positive cells relative to the negative control group are shown in FIG. 2B, and images of the senescent cells cultured in the presence of SB590885 are shown in FIG. 2C. As shown in FIGS. 2B and 2C, SB590885 is found to significantly reduce SA β-gal activity of the senescent cells.

3. Effect of SB590885 on Senescent Cells (1) Proliferation and SA β-Gal Activity of Senescent Cells Senescent cells are prepared as described in 1.

0.1 μM SB590885 is added to the prepared senescent cells, which are cultured in the presence of SB590885 for about 13 days. Cells treated with DMSO (Sigma-Adrich) alone are used as a negative control group.

Figure 3A:
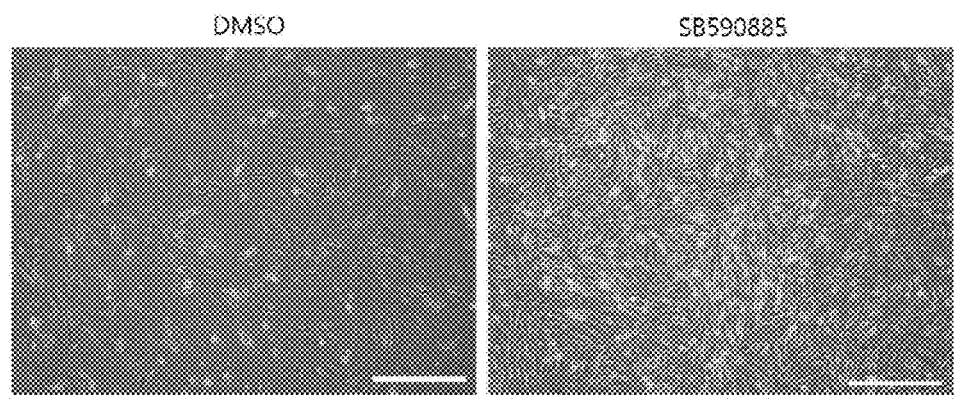
FIG. 3A shows staining images of senescent cells untreated ("0 day") or cultured in the presence of SB590885 for about 13 days (Scale bar: 1 mm)
Figure 3B:
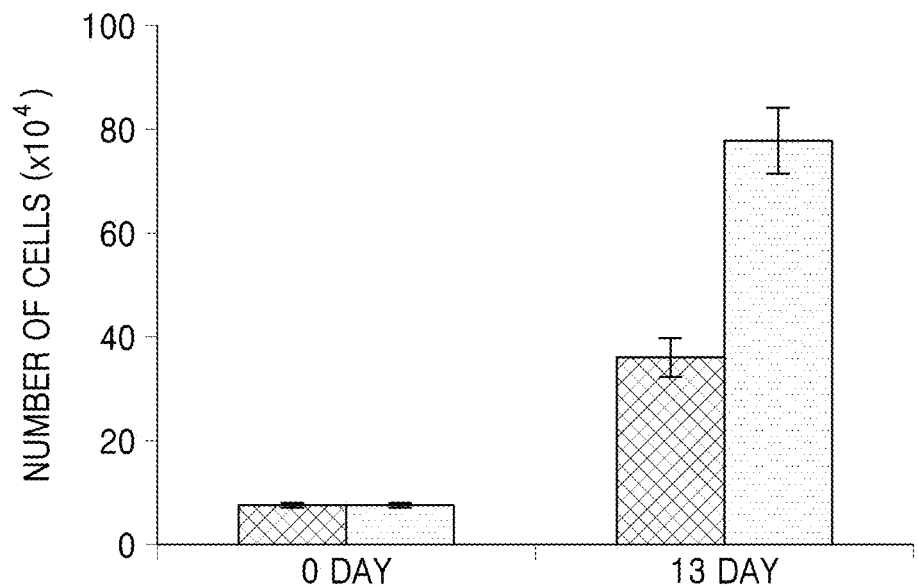
FIG. 3B is a graph showing the number of senescent cells cultured in the presence of SB590885 (▨: DMSO, ▦: SB590885)

The number of the senescent cells cultured in the presence of SB590885 for about 13 days is counted using a hemocytometer. Images of the cultured senescent cells are shown in FIG. 3A, and the number of the senescent cells cultured in the presence of SB590885 for about 13 days relative to that of the negative control group is shown in FIG. 3B (▨: DMSO, ▩: SB590885).

As shown in FIGS. 3A and 3B, the number of senescent cells cultured in the presence of SB590885 for about 13 days is about twice the number of cells in the negative control group.

(2) Quantity of Lipofuscin, Reactive Oxygen Species, and Lysosome in Senescent Cells In senescent cells, lipofuscin is accumulated, mitochondria are damaged by reactive oxygen species, and the number of lysosomes is increased. We therefore examined whether treatment of senescent cells with SB590885 affected these phenotypic markers of senescence.

As described in 1, 0.1 μM SB590885 is added to the prepared senescent cells, which are cultured in the presence of SB590885 for about 3 weeks. Cells treated with DMSO (Sigma-Adrich) alone are used as a negative control group.

Figure 4A:
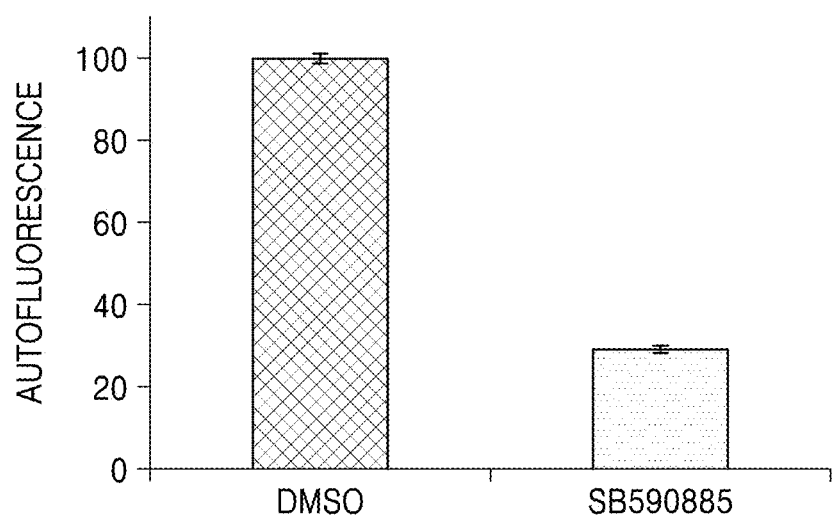
FIGS. 4A through 4C are graphs each showing a percentage of lipofuscin (%), reactive oxygen species (%), or lysosome (%) in cells cultured in the presence of SB590885 relative to a negative control group cultured in the presence of DMSO alone (▨: DMSO, ▦: SB590885)

As lipofuscin in senescent cells emits autofluorescence, accumulation of lipofuscin is analyzed by measuring the fluorescent radiation having a wavelength of 520 nm while irradiating the senescent cells with rays having a wavelength at about 488 nm using a FACSCaliber (Beckton Dickson). A relative autofluorescence ratio of the senescent cells cultured in the presence of SB590885 to the negative control group is calculated. The calculated autofluorescence ratio (%) is shown in FIG. 4A. As shown in FIG. 4A, the senescent cells cultured in the presence of SB590885 showed about 28% autofluorescence, which represents a 70% decrease in lipofuscin as a function of autofluorescence, compared to the negative control group.

Figure 4B:
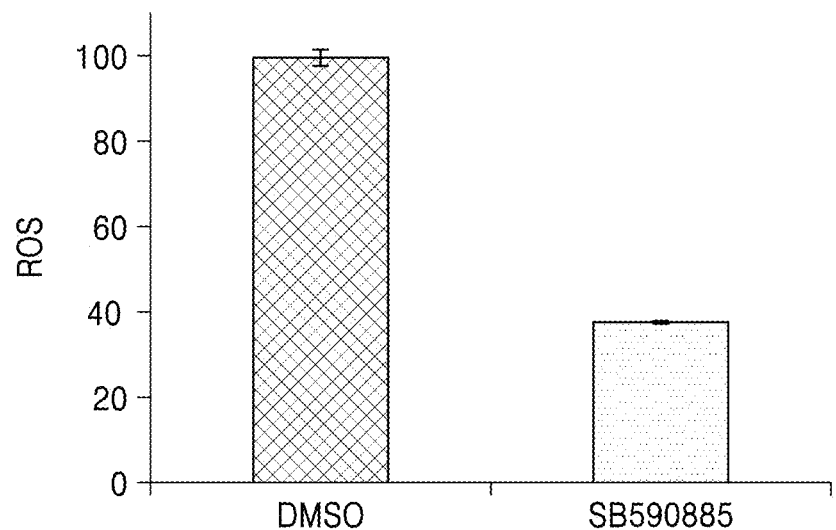

In order to measure mitochondrial function in senescent cells, the amount of reactive oxygen species (ROS) in the prepared senescent cells is measured using a MitoSOX™ Red Mitochondrial Superoxide indicator (Life technologies). A relative ROS amount of the senescent cells cultured in the presence of SB590885 to that of the negative control group is shown in FIG. 4B. As shown in FIG. 4B, the senescent cells cultured in the presence of SB590885 showed about 38% ROS, which represents about 60% decrease in the amount of ROS compared to the negative control group. Accordingly, SB590885 inhibits mitochondrial damage in senescent cells.

Figure 4C:
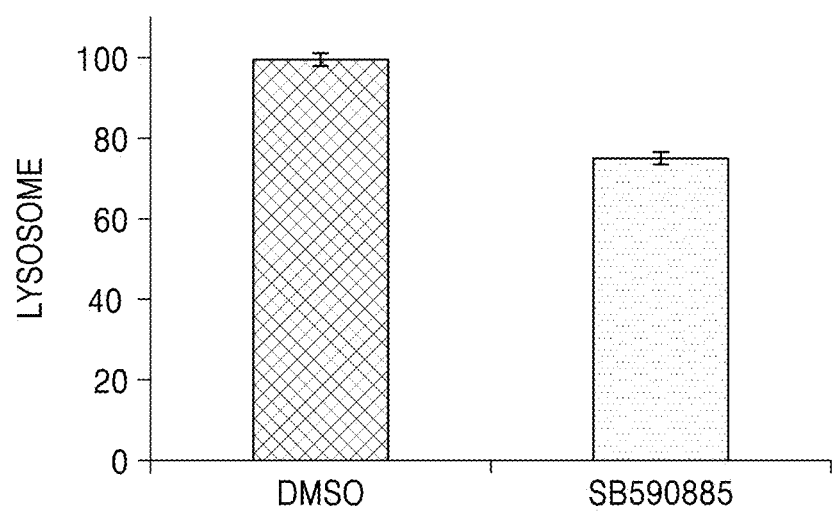

In order to measure lysosome accumulation in senescent cells, the prepared senescent cells are stained using a LysoTracker®Blue DND-22 (Life Technologies, Cat. No. L-7525). The amount of lysosome is quantified by measuring the fluorescent radiation having a wavelength of 422 nm while irradiating the stained senescent cells with rays having a wavelength at about 373 nm using a FACSCaliber (Beckton Dickson). The amount (%) of lysosome in the cells cultured in the presence of SB590885 relative to that of the negative control group is shown in FIG. 4C. As shown in FIG. 4C, the senescent cells cultured in the presence of SB590885 showed about 25% decrease in lysosome accumulation, compared to the negative control group.

Therefore, it is confirmed that SB590885 removes lipofuscin accumulation, recovers mitochondria damage, and reduces lysosome accumulation in senescent cells, thereby reducing the senescence level of senescent cells.

4. Effect of TAK-632 on Senescent Cells

The effect of TAK-632 treatment on markers of senescence was examined.

As described in 1, 0.1 μM TAK-632 is added to the prepared senescent cells, which are cultured in the presence of TAK-632 for about 3 weeks. Cells treated with DMSO (Sigma-Adrich) alone are used as a negative control group.

Figure 5A:
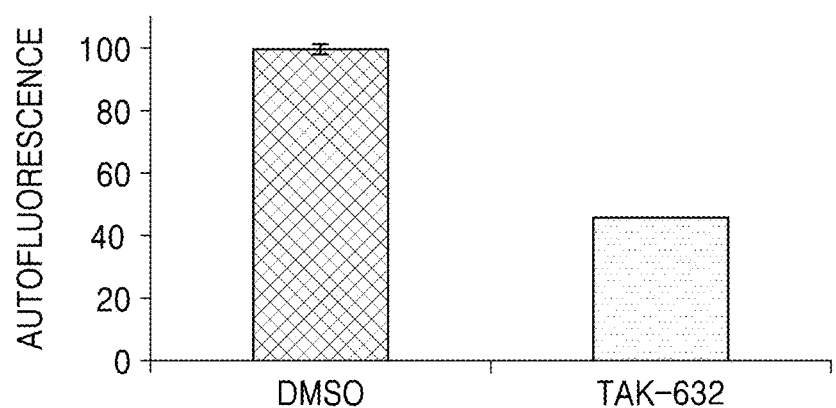
FIGS. 5A through 5C are graphs each showing a percentage of lipofuscin (%), reactive oxygen species (%), or lysosome (%) in cells cultured in the presence of TAK-632 to that of a negative control group (▨: DMSO, ▦: TAK-632)

As described in 3(2), autofluorescence in the senescent cells is measured and a relative autofluorescence ratio of the senescent cells cultured in the presence of TAK-632 to the negative control group is calculated. The calculated autofluorescence ratio (%) is shown in FIG. 5A. As shown in FIG. 5A, the senescent cells cultured in the presence of TAK-632 showed about a 48% decrease in lipofuscin, compared to the negative control group.

Figure 5B:
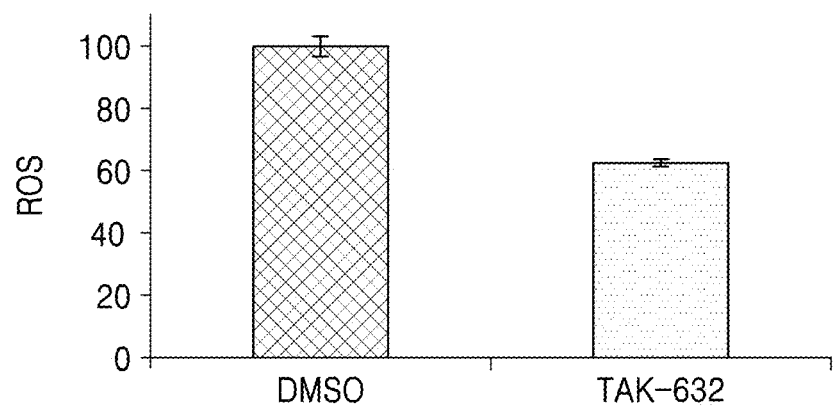

As described in 3(2), the amount of ROS in the senescent cells is measured. A relative ROS ratio of the senescent cells cultured in the presence of TAK-632 to the negative control group is calculated. The calculated ROS (%) is shown in FIG. 5B. As shown in FIG. 5B, the senescent cells cultured in the presence of TAK-632 showed about a 40% decrease in the amount of ROS, compared to the negative control group. Accordingly, it is found that mitochondria in the senescent cells are recovered from damage by TAK-632.

Figure 5C:
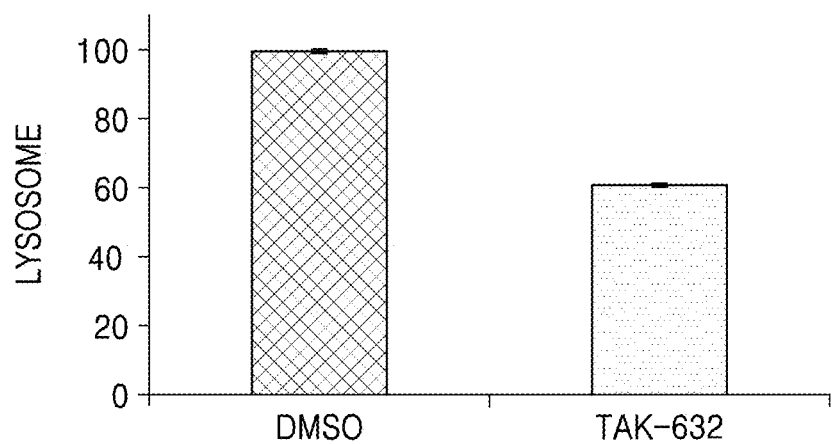

As described in 3(2), the amount of lysosomes in senescent cells is measured and the amount (%) of lysosome in the cells cultured in the presence of TAK-632 relative to that of the negative control group is shown in FIG. 5C. As shown in FIG. 5C, the senescent cells cultured in the presence of TAK-632 showed about a 40% decrease in lysosome accumulation, compared to the negative control group.

Therefore, it is confirmed that TAK-632 decreases lipofuscin accumulation, recovers mitochondrial damage, and reduces lysosome accumulation in senescent cells, thereby reducing the senescence level of senescent cells.

5. Effect of Vemurafenib on Senescent Cells

The effect of vemurafenib treatment on markers of senescence was measured.

As described in 1, 0.1 µM vemurafenib is added to the prepared senescent cells, which are cultured in the presence of vemurafenib for about 3 weeks. Cells treated with DMSO (Sigma-Adrich) alone are used as a negative control group.

Figure 6A:
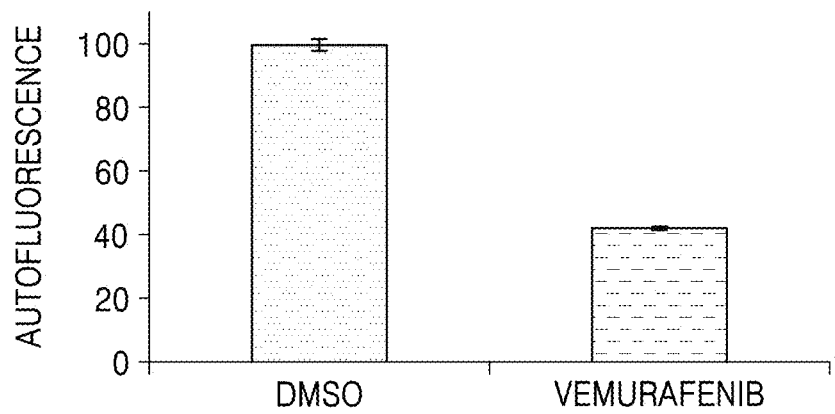
FIGS. 6A through 6C are graphs each showing a percentage of lipofuscin (%), reactive oxygen species (%), or lysosome (%) in cells cultured in the presence of vemurafenib to that of a negative control group (▨: DMSO, ▦: vemurafenib).

As described in 3.(2), autofluorescence in the senescent cells is measured and a relative autofluorescence ratio of the senescent cells cultured in the presence of vemurafenib to the negative control group is calculated. The calculated autofluorescence ratio (%) is shown in FIG. 6A. As shown in FIG. 6A, the senescent cells cultured in the presence of vemurafenib showed about 60% decrease in lipofuscin, compared to the negative control group.

Figure 6B:
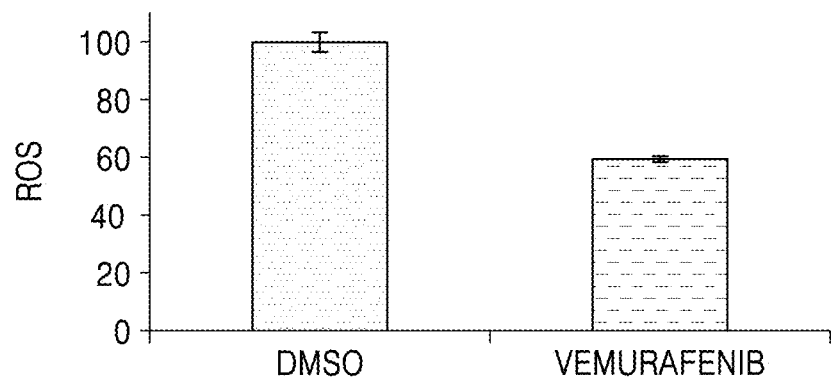

As described in 3.(2), the amount of ROS in the senescent cells is measured. A relative ROS ratio of the senescent cells cultured in the presence of vemurafenib to the negative control group is calculated. The calculated ROS (%) is shown in FIG. 6B. As shown in FIG. 6B, the senescent cells cultured in the presence of vemurafenib showed about 40% decrease in the amount of ROS, compared to the negative control group. Accordingly, it is found that mitochondria in the senescent cells are recovered from damage by vemurafenib.

Figure 6C:
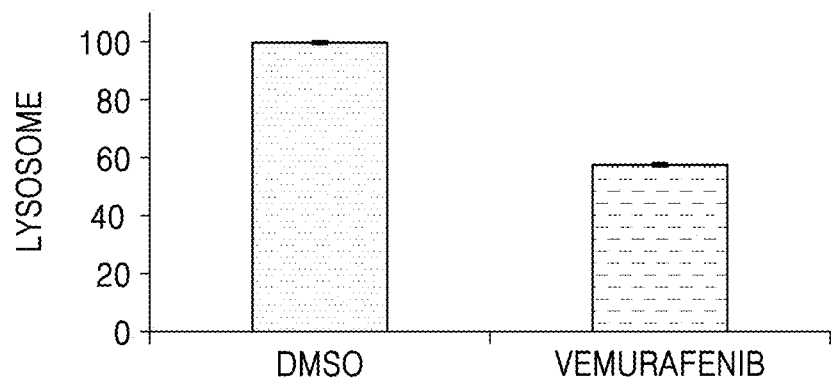

As described in 3.(2), the amount of lysosomes in senescent cells is measured and the amount (%) of lysosome in the cells cultured in the presence of vemurafenib relative to that of the negative control group is shown in FIG. 6C. As shown in FIG. 6C, the senescent cells cultured in the presence of vemurafenib showed about 40% decrease in lysosome accumulation, compared to the negative control group.

Therefore, it is confirmed that vemurafenib reduces lipofuscin accumulation, recovers mitochondrial damage, and reduces lysosome accumulation in senescent cells, thereby reducing the senescence level of senescent cells.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of reducing cellular senescence of a skin cell, comprising administering an effective amount of a BRAF inhibitor to the skin cell, wherein the BRAF inhibitor is SB590885, vemurafib, TAK-632, a pharmaceutically acceptable salt, stereomer, or solvate thereof, or a combination thereof.

2. The method of claim 1, wherein the skin cell is in a subject, and the method comprises administering the BRAF inhibitor to the subject.

3. The method of claim 1, wherein the administration is topical or systemic administration.

4. The method of claim 1, wherein the administration is topical administration to skin.

5. The method of claim 1, wherein the BRAF inhibitor is an agent inhibiting BRAF protein activity.

6. The method of claim 1, wherein reducing the cellular senescence of the skin cell comprises increasing cell proliferation, decreasing β-galactosidase activity, decreasing lipofuscin accumulation, decreasing formation of reactive oxygen species by mitochondria, or a combination thereof.

7. The method of claim 2, wherein the subject is afflicted by skin wrinkling, slow scar regeneration, degenerative alopecia, osteoporosis, sarcopenia, progeria, lysosome storage disease, or a combination thereof, caused by cellular senescence.

8. The method of claim 2, wherein the subject is afflicted with a disease caused by lipofuscin accumulation.

9. The method of claim 1, wherein the skin cell is a fibroblast.

* * * * *